(12) United States Patent
Grumm

(10) Patent No.: US 7,443,082 B2
(45) Date of Patent: Oct. 28, 2008

(54) PIEZOELECTRIC POLYMER COMPOSITE ARTICLE AND SYSTEM

(75) Inventor: Kipp O. Grumm, Grand Rapids, MI (US)

(73) Assignee: BASF Corporation, Florham Park, NJ (US)

( * ) Notice: Subject to any disclaimer, the term of this patent is extended or adjusted under 35 U.S.C. 154(b) by 108 days.

(21) Appl. No.: 11/276,508

(22) Filed: Mar. 3, 2006

(65) Prior Publication Data
US 2007/0205701 A1 Sep. 6, 2007

(51) Int. Cl.
*H01L 41/08* (2006.01)

(52) U.S. Cl. .................. 310/339; 310/357; 310/800

(58) Field of Classification Search ......... 310/363–366, 310/800
See application file for complete search history.

(56) References Cited

U.S. PATENT DOCUMENTS

| | | | |
|---|---|---|---|
| 4,296,349 A | | 10/1981 | Nakanishi et al. |
| 4,366,768 A | | 1/1983 | Kulischenko et al. |
| 4,434,114 A | | 2/1984 | Sprout, Jr. |
| 4,517,665 A | | 5/1985 | DeReggi et al. |
| 4,555,953 A | | 12/1985 | Dario et al. |
| 4,688,306 A | * | 8/1987 | Soni et al. ............... 29/25.35 |
| 4,786,837 A | | 11/1988 | Kalnin et al. |
| 4,805,157 A | | 2/1989 | Ricketts |
| 4,824,107 A | | 4/1989 | French |
| 4,835,747 A | | 5/1989 | Billet |
| 4,868,447 A | | 9/1989 | Lee |
| 4,877,988 A | | 10/1989 | McGinniss et al. |
| 4,904,222 A | * | 2/1990 | Gastgeb et al. ............ 446/405 |
| 5,128,581 A | | 7/1992 | Nakayama et al. |
| 5,172,024 A | * | 12/1992 | Broussoux et al. ...... 310/323.21 |
| 5,283,835 A | | 2/1994 | Athanas |
| 5,336,959 A | * | 8/1994 | Park et al. ................. 310/328 |
| 5,367,500 A | | 11/1994 | Ng |

(Continued)

FOREIGN PATENT DOCUMENTS

EP  1 044 466  3/2003

(Continued)

OTHER PUBLICATIONS

PCT International Search Report (International Application No. PCT/EP2007/051839).

*Primary Examiner*—Mark Budd
(74) *Attorney, Agent, or Firm*—Fernando A. Borrego; Howard & Howard

(57) ABSTRACT

The subject invention provides composite articles (20, 120) and associated systems (32, 132). A first composite article (20) includes a piezoelectric layer (22) having a piezoelectric property. The piezoelectric layer (22) is sandwiched between a first conductive layer (28) and a second conductive layer (30). At least one of the conductive layers (28, 30) is a conductive polymer having an electrically conductive property. A second composite article (120) includes first and second piezoelectric layers (122, 124) having a piezoelectric property. The first and second piezoelectric layers sandwich an insulating layer (126). A first system (32) and a second system (132) each include a control device (34) electrically connected to the first composite article (20) or the second composite article (120), respectively. The control device (34) measures an electrical signal generated by the respective piezoelectric layers (22, 122, 124) and/or produces an electrical signal to actuate the respective piezoelectric layers (22, 122, 124).

8 Claims, 5 Drawing Sheets

U.S. PATENT DOCUMENTS

| | | |
|---|---|---|
| 5,440,194 A | 8/1995 | Beurrier |
| 5,656,882 A | 8/1997 | Lazarus et al. |
| 5,760,530 A | 6/1998 | Kolesar |
| 5,797,623 A | 8/1998 | Hubbard |
| 5,911,158 A | 6/1999 | Henderson et al. |
| 5,951,908 A | 9/1999 | Cui et al. |
| 6,249,076 B1 | 6/2001 | Madden et al. |
| 6,492,762 B1 | 12/2002 | Pant et al. |
| 6,543,110 B1 | 4/2003 | Pelrine et al. |
| 6,664,716 B2 | 12/2003 | Cuhat et al. |
| 6,700,314 B2 | 3/2004 | Cuhat et al. |
| 6,768,246 B2 | 7/2004 | Pelrine et al. |
| 2002/0050769 A1 | 5/2002 | Pelrine et al. |
| 2004/0008853 A1 | 1/2004 | Pelrine et al. |
| 2005/0063122 A1 | 3/2005 | Wang |

FOREIGN PATENT DOCUMENTS

| | | |
|---|---|---|
| EP | 1 403 212 A2 | 3/2004 |
| JP | 02103823 | 4/1990 |
| JP | 09294730 | 11/1997 |
| WO | WO 99/356701 | 7/1999 |
| WO | WO 01/06575 A1 | 1/2001 |
| WO | WO 01/06579 A2 | 1/2001 |
| WO | WO 2005/091396 A2 | 9/2005 |

* cited by examiner

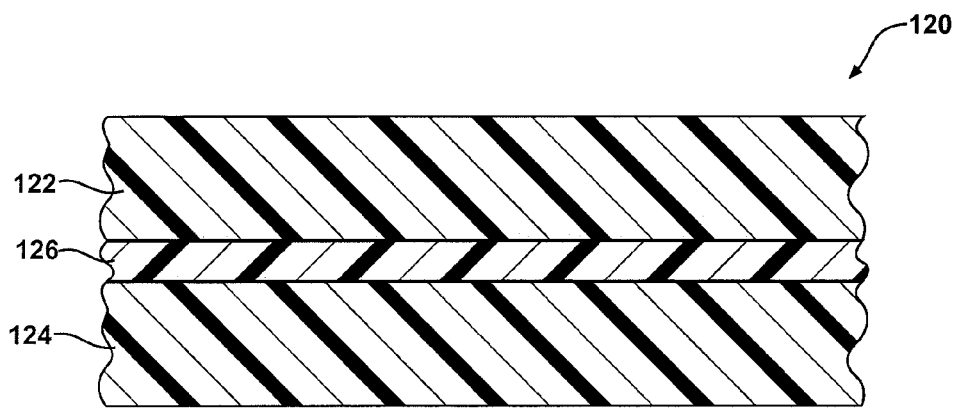
FIG - 5
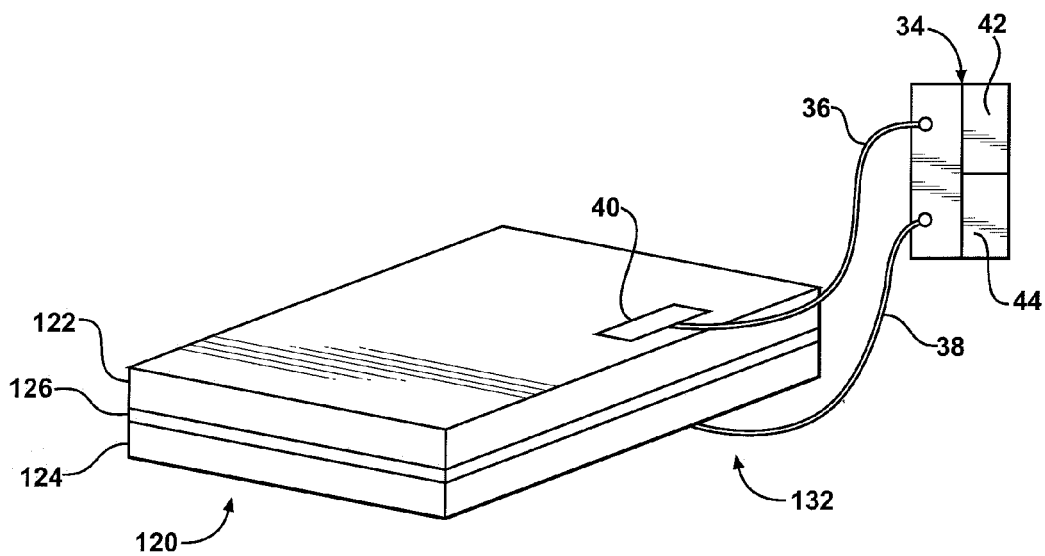
FIG - 6
FIG - 7
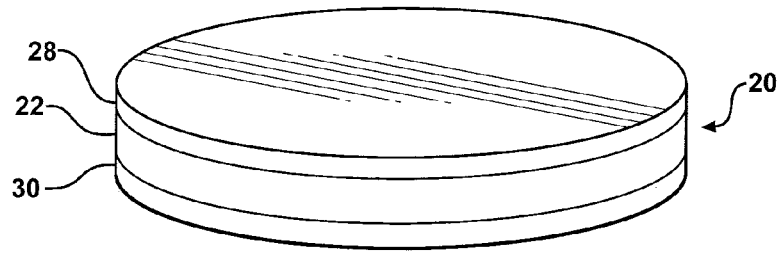

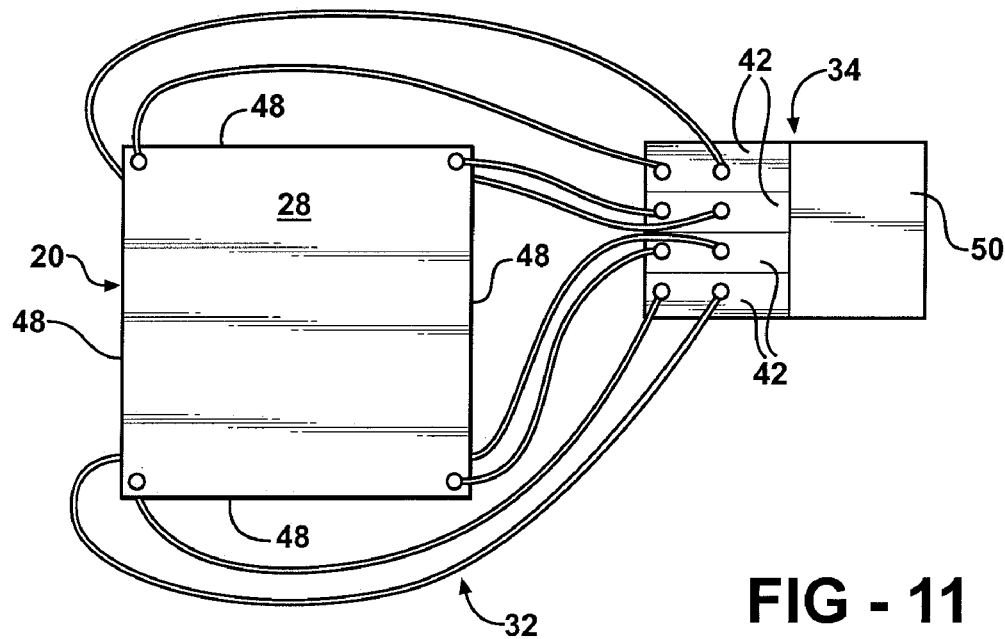
FIG - 11
FIG - 12
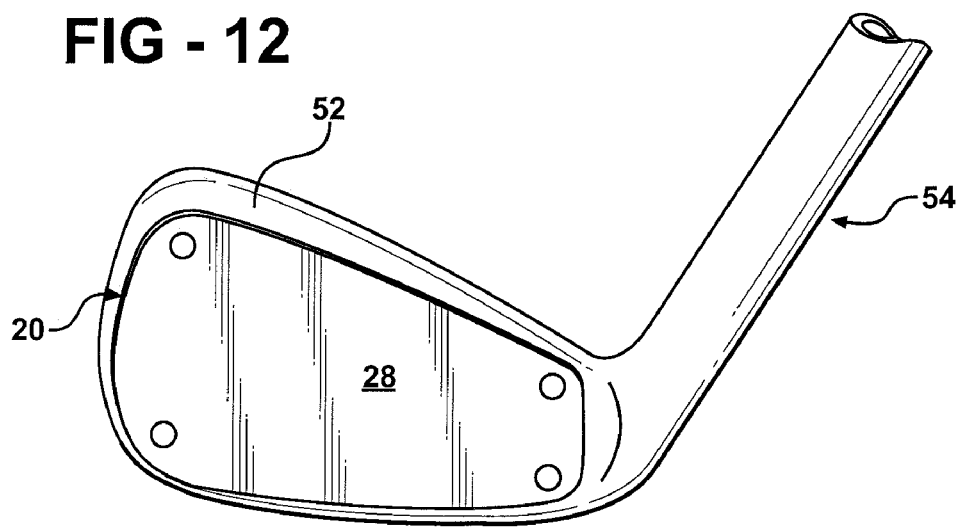

ated systems are well known in the art. Examples of
PIEZOELECTRIC POLYMER COMPOSITE ARTICLE AND SYSTEM

BACKGROUND OF THE INVENTION

1. Field of the Invention

The subject invention generally relates to composite articles having a piezoelectric layer. More specifically, the subject invention relates to composite articles having a piezoelectric layer formed of a polymer. The subject invention also relates to systems associated with the composite articles.

2. Description of the Related Art

Various articles having piezoelectric polymer layers and associated systems are well known in the art. Examples of such articles and systems are disclosed in U.S. Pat. No. 5,283,835 (the '835 patent).

The '835 patent discloses an article having a piezoelectric layer, preferably formed of a polymer such as polyvinylidine difluoride (PVDF). The piezoelectric layer is sandwiched between a pair of copper layers. Each conductive layer is overlayed by a nickel layer. The nickel layers are necessary to protect the copper layers from oxidation. The article of the '835 patent is deficient due to the nickel layer which adds complexity and reduces the flexibility of the article.

Furthermore, articles having piezoelectric layers sandwiched by metal layers tend to be cost prohibitive for a great many potential applications. Therefore, there remains an opportunity to provide articles which exhibit a piezoelectric property, resist oxidation, are flexible, and are cost efficient.

SUMMARY OF THE INVENTION AND ADVANTAGES

The subject invention provides a first composite article including a piezoelectric layer having a piezoelectric property. The piezoelectric layer defines a first side and a second side. A first conductive layer is disposed in contact with the first side of the piezoelectric layer. This first conductive layer comprises a first conductive polymer having an electrically conductive property.

The subject invention also provides a first system including the piezoelectric layer having a piezoelectric property. The piezoelectric layer defines the first side and the second side. The first conductive layer is disposed in contact with the first side of the piezoelectric layer and comprises a first conductive polymer having an electrically conductive property. A second conductive layer is disposed in contact with the second side of the piezoelectric layer and has an electrically conductive property. The first system also includes a control device electrically connected to the first conductive layer and the second conductive layer.

The subject invention provides a second composite article including a first piezoelectric layer and a second piezoelectric layer. The first and second piezoelectric layers each have a piezoelectric property and include electrically conductive material. An insulating layer is sandwiched between the first and second piezoelectric layers.

The subject invention further provides a second system including the second composite article and a control device. The control device is electrically connected to the first piezoelectric layer and the second piezoelectric layer.

The composite articles of the subject invention are highly resistive to oxidation. In the first composite article, the first conductive layer is a polymer and not a corrosive metal, such as copper. This negates the need for an additional layer (such as nickel) overlaying the first conductive layer to resist oxidation or the use of a conductive layer formed of a rigid, non-corrosive metal to be used (such as aluminum). Additionally, the use of a polymer as the first conductive layer is more cost efficient than the use of metals. This opens up new uses for the composite article that were previously cost prohibitive. Also, the polymer of the first conductive layer is flexible, allowing for use in a wide variety of applications requiring a flexible material. The second composite article likewise does not include any corrosive metals.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 5 is a cross-sectional view of a second composite article having an insulating layer sandwiched by a first piezoelectric layer and a second piezoelectric layer, in which each layer comprises a polymer;

FIG. 6 is a schematic view of a second system showing the second composite article electrically connected to the control device;

FIG. 7 is a perspective view of the first composite article with each layer having a circular shape;

FIG. 11 is a schematic view of the first composite article system with the control device including a plurality of meters and a processor;

FIG. 12 is a perspective view of a head of a golf club in combination with the first composite article;

DETAILED DESCRIPTION OF THE INVENTION

Referring to the Figures, wherein like numerals indicate corresponding parts throughout the several views, a first composite article is generally shown at 20.

Figure 1:
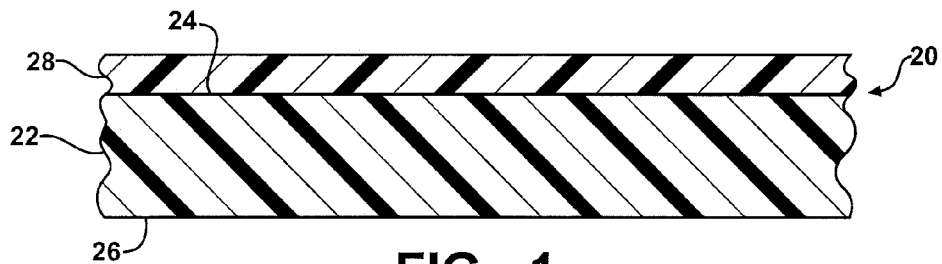
FIG. 1 is a cross-sectional view of a first composite article having a piezoelectric layer and a first conductive layer comprising a first conductive polymer.

Referring to FIG. 1, the first composite article 20 includes a piezoelectric layer 22 having a piezoelectric property or piezoelectric properties. As is well known to those skilled in the art, a substance with piezoelectric properties generates an electrical voltage in response to applied mechanical strain or stress. Likewise, the substance with piezoelectric properties will mechanically deform in response to an applied electric field. A substance with piezoelectric properties is also referred to by those skilled in the art as having ferroelectric properties.

Preferably, the piezoelectric layer 22 is formed from a polymer having piezoelectric properties. Most preferably, the polymer is polyvinylidine difluoride (PVDF). One manufacturing method for increasing the piezoelectric properties of a PVDF material is known to those skilled in the art. First, the monomers of the PVDF are aligned in the preferred direction by stretching the material in the proper ratio. The material is then heated and exposed to a large electric field, which allows the monomer's to arrange themselves in the poled direction. Once the material is cooled, the monomers retain their poled direction, giving the material a net dipole moment made up of the net effect of the many poled monomers. Essentially, this process aligns the fluorine atoms on one side of the carbon backbone of the PVDF molecule, giving the material a strong dipole moment which is sensitive to applied pressure, giving a change in the voltage drop across upper and lower faces of a sheet of the PVDF polymer.

Those skilled in the art realize that other polymers that exhibit piezoelectric properties may also be used as the piezoelectric layer 22. Futhermore, other non-polymer substances that exhibit piezoelectric properties may be used as the piezoelectric layer 22, such as, but not limited to, quartz crystals, ceramics with perovskite, and tungsten-bronze structures.

The piezoelectric layer 22 defines a first side 24 and a second side 26. A first conductive layer 28 is disposed in contact with the first side 24 of the piezoelectric layer 22. The first conductive layer 28 is a polymer having an electrically conductive property or electrically conductive properties (i.e., a conductive polymer). In other words, the first conductive layer 28 is able to conduct an electric current. Preferably, the first conductive layer 28 is formed of nylon and includes carbon nanotubes. The first conductive layer 28 preferably includes a 20% concentration of double-walled carbon nanotubes, however other concentrations may also be suitable. One suitable polymer for the first conductive layer 28 is Ultramid® A3WC4 manufactured by BASF Aktiengesellschaft headquartered in Ludwigshafen am Rhein, Germany. Of course, those skilled in the art realize other suitable polymers having electrically conductive properties may be used.

Those skilled in the art of further realize that the double-walled carbon nanotubes are currently the most commercially available type of carbon nanotube. However, single-wall carbon nanotubes, which are reported to be as conductive as copper, or approximately 10,000 times more conductive that the double-wall nanotubes, may also be suitable. Furthermore, research is ongoing to obtain carbon nanotubes that have been embedded with metal atoms (such as nickel), which again make the nanotubes even more conductive. Obviously, when these types of carbon nanotubes and related nanotechnological enhancements come in to fruition, they may be substituted for the double-walled carbon nanotube in the first conductive layer 28 depending on the desired conductivity.

The first composite article 20, with the piezoelectric layer 22 and the first conductive layer 28 being polymers, is highly resistive to corrosion and oxidation. Therefore, the first composite article 20 will not rust and structurally decay in moist, humid, or wet environments Furthermore, the first composite article 20 retains the flexibility of a polymer. Moreover, the overall cost of the first composite article 20 is less than the cost of a metallic layer being applied to the piezoelectric layer 22.

Figure 2:
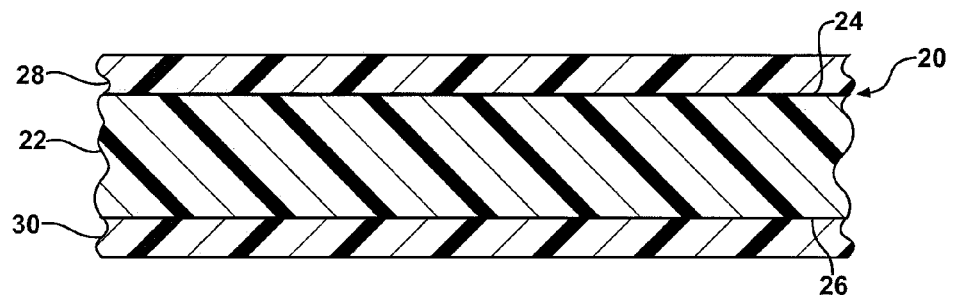
FIG. 2 is a cross-sectional view the first composite article having the piezoelectric layer sandwiched by the first conductive layer and a second conductive layer, in which both conductive layers are conductive polymers.

Referring to FIG. 2, a preferred embodiment of the first composite article 20 includes a second conductive layer 30 disposed in contact with the second side 26 of the piezoelectric layer 22. The second conductive layer 30 has electrically conductive properties. Preferably, the second conductive layer 30 is formed from a second conductive polymer having electrically conductive properties. As with the first conductive layer 28, the second conductive layer 30 is preferably formed of nylon and includes carbon nanotubes, such as, but not limited to, the BASF Ultramid® A3WC4.

Figure 3:
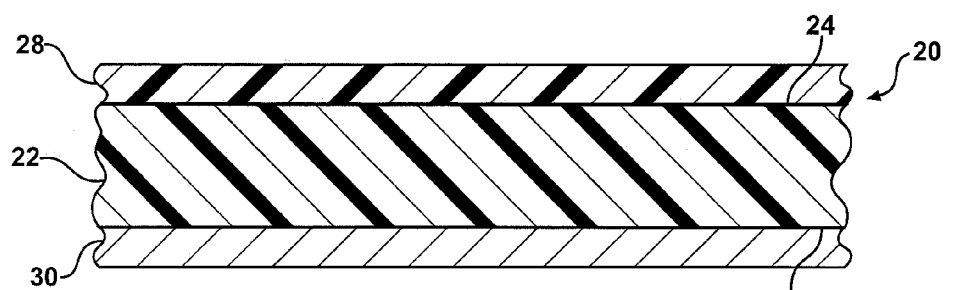
FIG. 3 is a cross-sectional view of the first composite article having the piezoelectric layer sandwiched by the first conductive layer and the second conductive layer, in which the first conductive layer comprises a first conductive polymer and the second conductive layer comprises a metal.

Alternatively, referring to FIG. 3, the second conductive layer 30 is formed from a metal which is electrically conductive. Numerous metals may be used to form the second conductive layer 30, including, but not limited to, gold, silver, copper, and aluminum. One common practice for forming the metallic second conductive layer 30 is to coat the second side 26 of the piezoelectric layer 22 with a conductive silver paint. Of course, other acceptable practices are known to those skilled in the art Referring now to FIG. 4, the subject invention also includes a first system 32. The first system 32 includes the piezoelectric layer 22 having piezoelectric properties sandwiched by the first conductive layer 28 formed of a first conductive polymer and the second conductive layer 30, as described above. Preferably, the second conductive layer 30 is formed from a second conductive polymer.

The first system 32 includes a control device 34 electrically connected to the first conductive layer 28 and the second conductive layer 30. Numerous techniques for electrically connecting the control device 34 and the conductive layers 28, 30 are realized by those skilled in the art. One such technique is using a first wire 36 and a second wire 38 to electrically connect the first conductive layer 28 and the second conductive layer 30, respectively, to the control device 34. The wires 36, 38 may be affixed to the conductive layers 28, 30 using pieces of conductive tape 40. Suitable conductive tapes 40, include, but are not limited to, part nos. 9712 and 9713 manufactured by 3M Company, headquartered in St. Paul, Minn.

The control device 34 may include a meter 42 for receiving an electrical signal (i.e., an electrical voltage) produced by the piezoelectric layer 22 when the piezoelectric layer 22 is stressed or strained. Typically, the greater the stress or strain on the piezoelectric layer 22, the greater the magnitude of the electrical signal. The meter may receive the electrical signal for measuring the electrical signal (e.g., instrumentation purposes) or passing along the electrical signal (e.g., electrical power generation).

The control device 34 may alternatively include a power supply 44. The power supply 44 is electrically connected to the first conductive layer 28 and the second conductive layer 30 for applying an electrical signal to the conductive layers 28, 30. When the electrical signal is applied, the piezoelectric layer 22 is actuated (i.e., deflected, warped, etc.). When an electrical signal oscillating in polarity is applied to the conductive layers 28, 30, the piezoelectric layer 22 will also oscillate back and forth. When the oscillation is of a frequency associated with audible sound (i.e., approximately 20 Hz to 20 kHz), the piezoelectric layer 22 and the first composite article 20 vibrates to generate a sound, creating an audio speaker effect.

The control device 34 may include both the meter 42 and the power supply 44. Furthermore, the control device 34 may include a plurality of meters 42 and/or power supplies 44. The number of meters 42 and/or power supplies 44 that may incorporated within the control device 34 is based on the particular application of the first composite article 20.

Referring now to FIG. 5, the subject invention also includes a second composite article 120. The second composite article 120 includes a first piezoelectric layer 122 having piezoelectric properties. The first piezoelectric layer 122 preferably comprises a polymer and most preferably comprises PVDF. Of course, those skilled in the art realize that other polymers or non-polymers exhibiting piezoelectric properties may be employed as the first piezoelectric layer 122.

The first piezoelectric layer 122 of the second composite article 120 includes electrically conductive material. Said another way, the first piezoelectric layer is doped with the electrically conductive material. This electrically conductive material is preferably carbon nanotubes. Both double-walled and single-walled carbon nanotubes may be utilized as the electrically conductive material.

The second composite article 120 also includes a second piezoelectric layer 124. As with the first piezoelectric layer 122, the second piezoelectric layer 124 has piezoelectric properties and includes electrically conductive material. It is most preferred that the second piezoelectric layer 124 comprise PVDF doped with carbon nanotubes.

Of course, each piezoelectric layer 122, 124 need not be comprise the same material or include the same conductive material as the other piezoelectric layer 124, 122 (i.e., the piezoelectric layers 122, 124 need not be identical in composition to one another).

The second composite article 120 includes an insulating layer sandwiched 126 between the first and second piezoelectric layers 122, 124. The insulating layer electrical insulates (i.e., isolates) the first piezoelectric layer 122 from the second piezoelectric layer 124. Preferably, the insulating layer 126 comprises a polymer and most preferably, the insulating layer comprises PVDF. However, those skilled in the art realize that the piezoelectric properties of the insulating layer 126, if any, are much less than the piezoelectric properties of the piezoelectric layers 122, 124. Furthermore, those skilled in the art realize other electrically insulating materials could be implemented as the insulating layer 126, including, but not limited to, rubbers or ceramics.

When stressed, a positive charge will be generated on one of the piezoelectric layers 122, 124 of the second composite material 120 while a negative charge will be generated on the other of the piezoelectric layers 124, 122. The insulating layer 128 prevents the positive and negative charges from canceling each other out.

As shown in FIG. 6, the subject invention also includes a second system 132. The second system 132 includes the first and second piezoelectric layers 122, 124 having piezoelectric properties sandwiching an insulating layer 128, as described above as the second composite article 120.

The second system 132 includes the control device 34 described above. The control device 34 is electrically connected to the first piezoelectric layer 122 and the second piezoelectric layer 124. As with the first system 32, numerous techniques for electrically connecting the control device 34 and the piezoelectric layers 122, 124 of the second system 132 are realized by those skilled in the art.

Numerous variations and exemplary applications of the composite articles 20, 120 and systems 32, 132 may be practiced within the scope of the subject invention. Several of these variations and exemplary applications are described in greater detail below. These descriptions are, for convenience purposes, in terms of the first composite article 20 and/or the first system 32. However, these variations, exemplary applications, and other teachings are equally applicable to the second composite article 120 and/or second system 132, and should not be perceived of as limited the first composite article 20 and first system 120.

Figure 4:
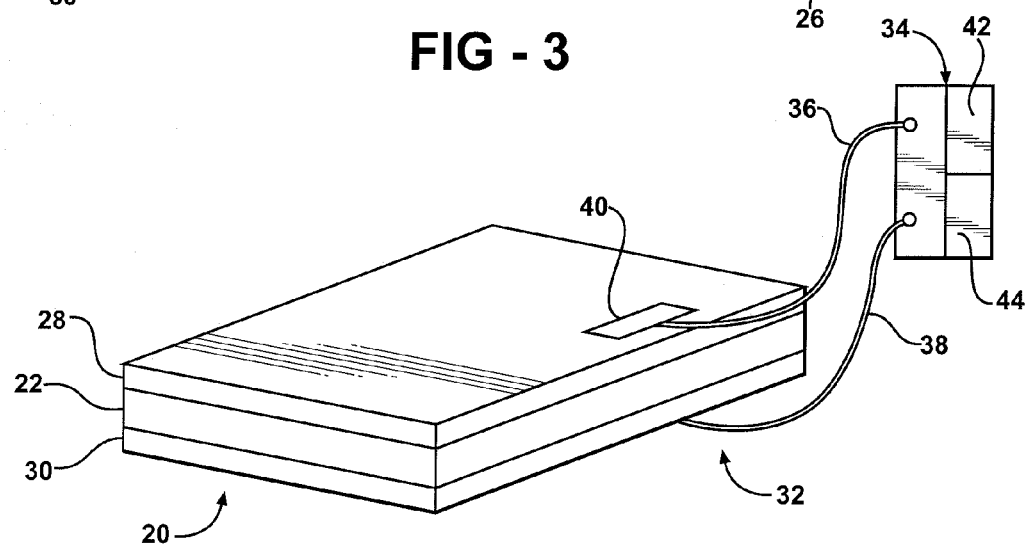
FIG. 4 is a schematic view of a first system showing the first composite article electrically connected to a control device.
Figure 8:
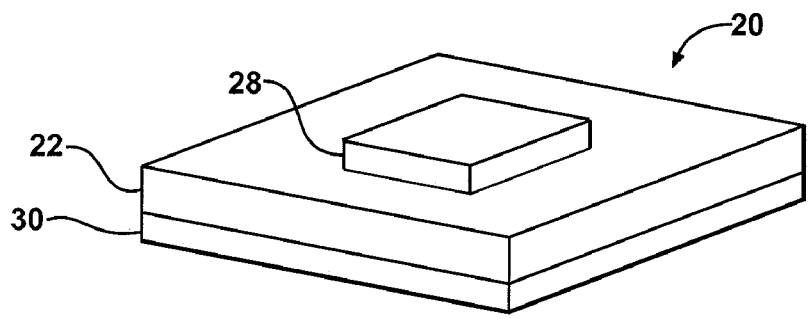
FIG. 8 is a perspective view of the first composite article with the first conductive layer being having a smaller surface area than the piezoelectric layer and the second conductive layer.

FIG. 4 portrays each of the layers 22, 28, 30 as each having a rectangular shape, having of substantial equal surface areas, and being disposed centered with respect to one another. However, each layer may be of other shapes, have different sized surface areas, and need not be disposed centered with respect to one another. The shape, size, and positional disposition of the layers 22, 28, 30 will be typically based on the particular application of the first composite article 20. For example, FIG. 7 shows the first composite article 20 with each of the layers 22, 28, 30 having a circular shape. FIG. 8 shows the first composite article 20 where the first conductive layer 28 has a surface area smaller than a surface area of the piezoelectric layer 22 and the second conductive layer 30.

Figure 9:
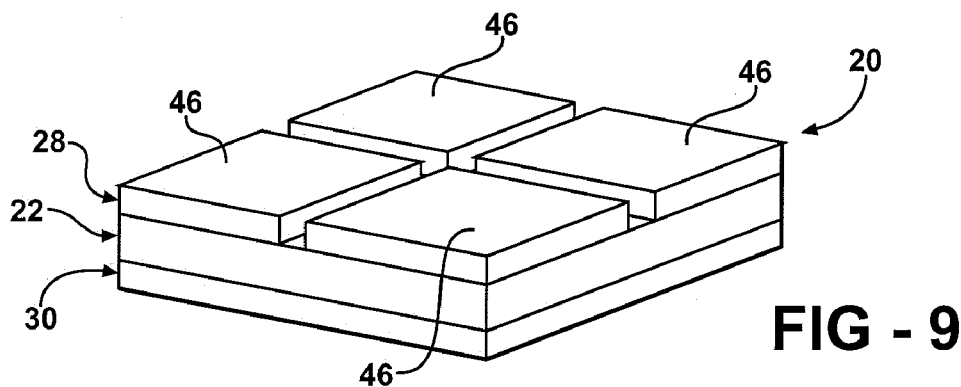
FIG. 9 is a perspective view of the first composite article with the first conductive layer segmented in a plurality of conductive sections.
Figure 10:
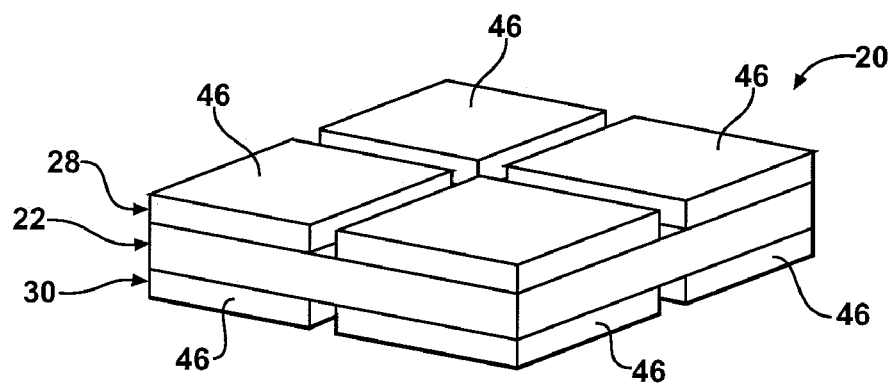
FIG. 10 is a perspective view of the first composite article with both the first and second conductive layers segmented in a plurality of conductive sections.

Referring now to FIGS. 9 and 10, the first conductive layer 28 may be segmented into a plurality of conductive sections 46. The conductive sections 46 are electrically insulated from each other. In the case of the first composite article 20 shown in FIG. 9 and 10, air is an insulating material to electrically insulate the sections; however those skilled in the art realize other insulating materials that may be acceptable. One possible application of having the first conductive layer 28 segmented into conductive sections 46 is to use the first system 32 to determine a location of an impact on the first composite article 20. Of course, those skilled in the art realize other possible applications for the segmented first conductive layer 28.

In FIG. 9, the second conductive layer 30 is shown a single piece, which provides a common circuit path for the plurality of conductive sections 46 of the first conductive layer 28. However, in FIG. 10, the second conductive layer 30 is shown segmented into a plurality of conductive sections 46, such that each conductive section 46 of the first conductive layer 28 provides a circuit path with a corresponding conductive section 46 of the second conductive layer 30.

Although segmenting the first conductive layer 28 into a plurality of conductive sections 46 is effective to determine the location of impact on the first composite article 20, the first system 32 may be used to determine the location of impact with the first conductive layer 28 being non-segmented (i.e., a contiguous piece). Referring to FIG. 11, in a first exemplary application of the first system 32, the first composite article 20 defines a periphery having at least three edges 48. The control device 34 includes at least three meters 42. The at least three meters 42 are electrically connected to the first and second conductive layers 28, 30 at separate locations along the periphery. Preferably, the electrical connections are proximate to where the edges 48 meet (i.e., the vertices of the composite article 20. It is also preferred that the number of meters 42 is equal to the number of vertices of the first conductive layer 28. Although FIG. 9 shows the first system 32 with the composite article 20 having four vertices electrically connected to the control device 34 having four meters 42, those skilled in the art realize that alternate numbers of edges 48, vertices, and meters 42 may be acceptable. Those skilled in the art also realize that the at least three meters 42 of the control device 34 may share a single common feed to electrically connect the meters 42 to the second conductive layer 30.

The control device 34 of the first exemplary application of the first system 32 also includes a processor 50 electrically connected to the at least three meters 42. The processor 50 is preferably a microprocessor-based computing device. The processor 50 determines a compression point on the piezoelectric layers 22 based on the locations of the electrical connections along the periphery of the first conductive layer 28 and each electrical signal measured at each of the at least three meters 42. The processor 50 determines the compression point by comparing the magnitudes of the electrical signals (e.g., voltages) and performing a trilateration technique.

The first exemplary application of the first system 32 may be used as a golf training tool to determine the point of impact on the composite article 20, as shown in FIG. 12. The first composite article 20 may be shaped, sized, and affixed to a head 52 of a golf club 54. Those skilled in the art realize that the metallic head 52 of the golf club 54 may be alternatively used as the second conductive layer 30 of the first composite article 20. As the golf club 54 is swung and strikes a golf ball, the processor 50 (not shown in FIG. 10) then determines the point of impact on the head 52. The processor 50 may be in communication with a display (not shown), such as a display of a personal computer or personal digital assistant (PDA). The point of impact may then be shown on a graphical representation of the head 52 of the golf club 54. By seeing this visual evidence, a golfer may then be able to adjust his or her swing to find the optimal "strike-point" on the head 52 of the golf club 54.

Figure 13:
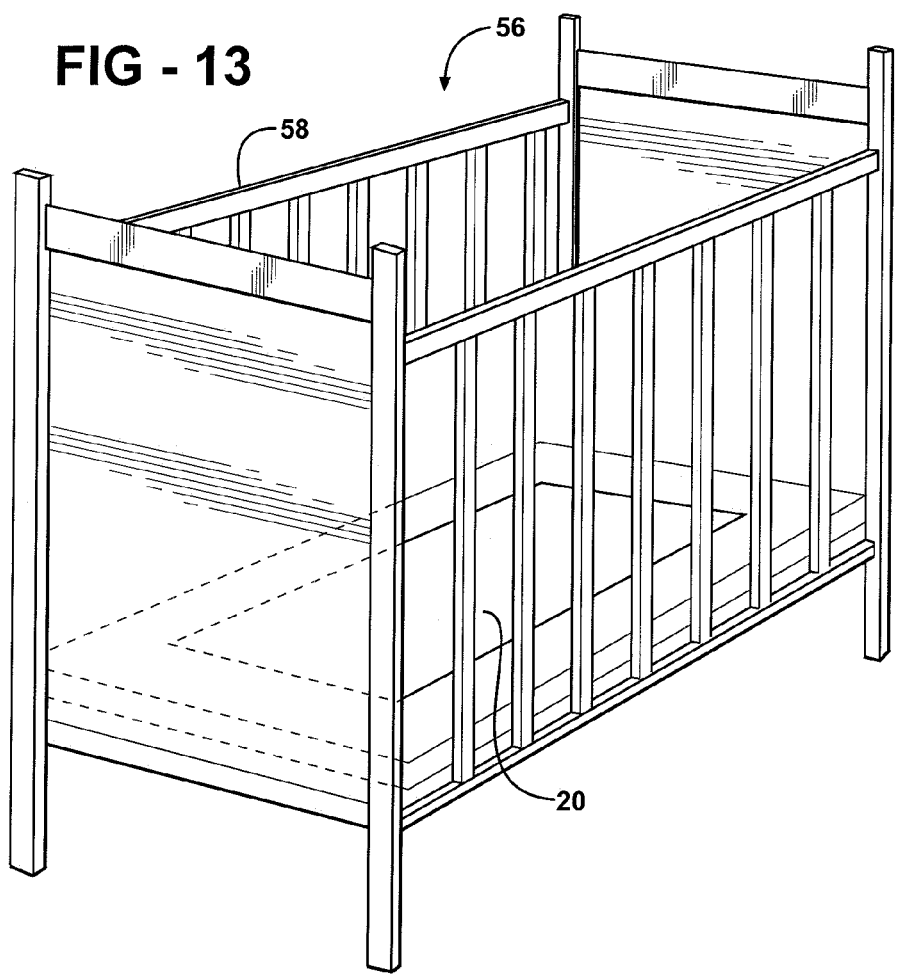
FIG. 13 is a perspective view of a crib in combination with the first composite article.

The first system 32 may also be used in combination with a bed 56 for monitoring breathing and/or movement of an individual. This second exemplary application would be useful in hospital environments to monitor the status of a patient. The application may also be used in a child's crib 58, as shown in FIG. 13, to monitor breathing and/or movement of an infant. For example, the first composite article 20 may be disposed on top of a mattress 60, as shown. Alternatively, the first composite article 20 may be disposed along the sides 24, 26 of the crib 58 (not shown). The piezoelectric layer 22 of the first composite article 20 is sensitive enough to produce the electrical signal even from the infant's breath. The processor 50 (not shown in FIG. 11) would monitor the breathing and/or movement of the infant and produce an alert signal if the breathing and/or movement should cease. The alert signal may then be transmitted to a remote monitor to alert parents or other caregivers as to the condition of the infant. Obviously, this application of the first composite article 20 and first system 32 would have great benefits in monitoring the infant's health and helping to prevent death due to sudden infant death syndrome (SIDS).

Figure 14:
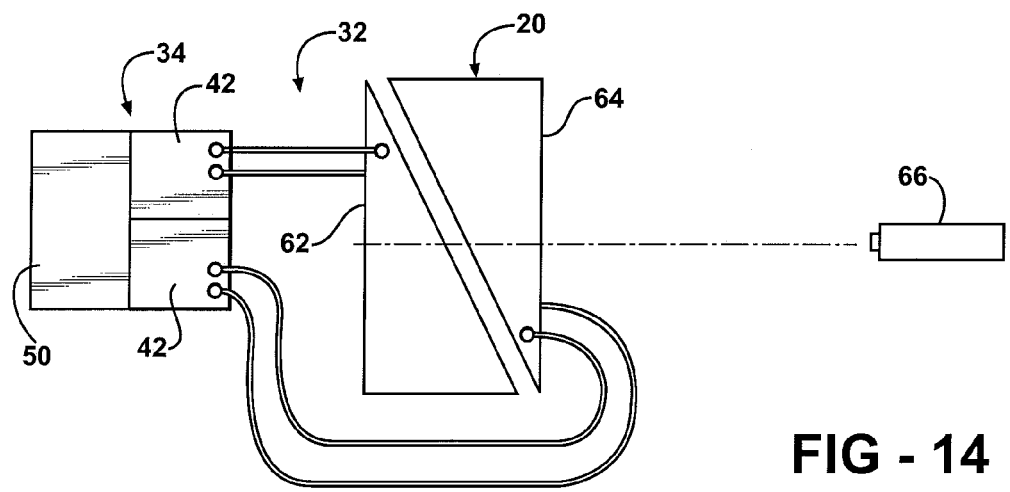
FIG. 14 is a schematic view of the first system having a pair of composite article segments for sensing a height of a sweeping laser beam.

Referring now to FIG. 14, a third exemplary application of the first system 32 is a laser position sensor. In this application, the first system 32 includes a first segment 62 of the first composite article 20 and a second segment 64 of the first composite article 20 disposed adjacent to each other. Preferably, each of the segments 62, 64 is identical in size and shaped as a right triangle. Hypotenuses of the right triangle-shaped segments 62, 64 are disposed adjacent to each other, yet separated to electrically isolate the segments 62, 64 from each other. The control device 34 includes a pair of meter's 42 with each meter 42 electrically connected to one of the segments 62, 64 of the composite article 20. The electrical connection of one of the meters 42 is disposed generally at a high vertex of the first segment 62 and the electrical connection of the other meter 42 is disposed generally at a low vertex of the second segment 64. The control device 34 also includes the processor 50 electrically connected to each of the meters 42. A laser emitter 66 produces a sweeping laser beam which crosses both of the segments 62, 64. When the sweeping laser beam crosses the segments 62, 64, each piezoelectric layer 22 of each segment produces an electrical signal. The meters 42 read the electrical signal which is proportionate to the location of the connection to the meter 42 relative to the location of the sweeping laser beam. The processor 50 compares the electrical signals from each of the pair of meters 42 to determine the position (i.e., height) of the sweeping laser beam. This third exemplary application will find numerous uses in construction, surveying, and other industries.

The subject invention may also be used in a fourth exemplary application for a sound canceling device (not shown). The sound canceling device includes a first part of the first composite article 20 and a second part of the first composite article 20 separate and electrically isolated from the first part. The control device 34 includes the meter 42 electrically connected to the conductive layers 28, 30 of the first part of the first composite article 20. The meter 42 senses a first electrical signal produced by sound vibrating the piezoelectric layer 22 of the first part of the first composite article 20. The control device 34 also includes an inverter circuit electrically connected to the meter 42. The inverter circuit receives the first electrical signal and produces a second electrical signal having inverse properties of the first electrical signal. Of course, the inverter circuit may be implemented as the processor 50. The control device 34 further includes the power supply 44 electrically connected to the inverter circuit and the conductive layers 28, 30 of the second part of the composite article 20. The control device 34 receives the second electrical signal and actuates the piezoelectric layer 22 of the second part in accordance with the second electrical signal. This actuation of the second electrical signal, which is an inverse of the first electrical signal, cancels sound received by the piezoelectric layer 22 of the first part. Numerous implementations of the fourth exemplary embodiment exist, including, but not limited to, airplanes, office dividers, walls, sound studios, and audio headphones.

A fifth exemplary application is the first composite article 20 in combination with a membrane pump (not shown) for pumping a fluid. The power supply 44 of the control device 34 provides an electrical signal to the first composite article 20, which in turn deflects to provide a gentle pumping motion. This fifth exemplary application may have applications in advanced medical devices, such as, artificial hearts.

Obviously, many modifications and variations of the present invention are possible in light of the above teachings. The invention may be practiced otherwise than as specifically described within the scope of the appended claims. In addition, the reference numerals in the claims are merely for convenience and are not to be read in any way as limiting.

What is claimed is:

1. A composite article (120) comprising;
    a first piezoelectric layer (122) having a piezoelectric property and comprising electrically conductive material,
    a second piezoelectric layer (124) having a piezoelectric property and comprising electrically conductive material, and
    an insulating layer (126) sandwiched between said first and second piezoelectric layers (122, 124).

2. A composite article (120) as set forth in claim 1 wherein said first and second piezoelectric layers (122, 124) comprise polymers having a piezoelectric property.

3. A composite article (120) as set forth in claim 1 wherein said first piezoelectric layer (122) comprises polyvinylidine difluoride (PVDF) having a piezoelectric property and said second piezoelectric layer (124) comprises PVDF having a piezoelectric property.

4. A composite article (120) as set forth in claim 1 wherein said electrically conductive material is further defined carbon nanotubes.

5. A composite article (120) as set forth in claim 1 wherein said insulating layer (126) comprises a polymer.

6. A composite article as set forth in claim 5 wherein said insulating layer (126) comprises polyvinylidine difluoride (PVDF).

7. A system (132) comprising;
a first piezoelectric layer (122) having a piezoelectric property and including electrically conductive material,
a second piezoelectric (124) layer having a piezoelectric property and including electrically conductive material,
an insulating layer (126) sandwiched by said first and second piezoelectric layers, and
a control device (34) electrically connected to said first piezoelectric layer (122) and said second piezoelectric layer (124).

8. A system (132) as set forth in claim 7 wherein said control device (34) is further defined as a meter (42) for receiving an electrical signal produced by said piezoelectric layers (122, 124).

* * * * *